US008469959B2

(12) United States Patent
Jacob et al.

(10) Patent No.: US 8,469,959 B2
(45) Date of Patent: Jun. 25, 2013

(54) BONE PREPARATION DEVICE (75) Inventors: Clinton R. Jacob, Germantown, TN (US); J Kenneth Burkus, Columbus, GA (US); Jared R. Shoup, Memphis, TN (US); Greg C. Marik, Collierville, TN (US); Newton H. Metcalf, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 319 days.

(21) Appl. No.: 12/703,867

(22) Filed: Feb. 11, 2010

(65) Prior Publication Data
US 2011/0196373 A1     Aug. 11, 2011

(51) Int. Cl.
*A61B 17/00*    (2006.01)
(52) U.S. Cl.
USPC ............ 606/79; 606/99; 606/86 R; 606/86 A
(58) Field of Classification Search
USPC ................... 606/79, 80, 83, 84, 90, 99, 86 A, 606/86 R
See application file for complete search history.

(56) References Cited

U.S. PATENT DOCUMENTS

| | | | | |
|---|---|---|---|---|
| 6,159,214 A | * | 12/2000 | Michelson | 606/80 |
| 7,153,303 B2 | * | 12/2006 | Squires et al. | 606/79 |
| 2003/0130662 A1 | * | 7/2003 | Michelson | 606/79 |
| 2003/0195517 A1 | * | 10/2003 | Michelson | 606/79 |
| 2007/0118145 A1 | * | 5/2007 | Fischer et al. | 606/99 |
| 2007/0270862 A1 | * | 11/2007 | Yu et al. | 606/79 |
| 2008/0195104 A1 | * | 8/2008 | Sidebotham et al. | 606/80 |
| 2010/0023066 A1 | | 1/2010 | Long et al. | |
| 2010/0145458 A1 | * | 6/2010 | Aferzon et al. | 623/17.16 |

* cited by examiner

*Primary Examiner* — Kevin T Truong
*Assistant Examiner* — Si Ming Lee (57) ABSTRACT

A bone preparation device for shaping endplates forming an intervertebral disc space between two adjacent vertebrae includes a cutter component and a cutter-positioner component. The cutter-positioner is arranged to limit the distal travel of the cutter component and to restrict the range of motion of the distal end of the cutter component. The bone preparation device also includes a rotational interface between the cutter component and the cutter-positioner component. The rotational interface is structurally arranged to permit the cutting blade to be rotated at the same time the cutter component is restricted in its range of motion.

12 Claims, 10 Drawing Sheets

BONE PREPARATION DEVICE

FIELD OF THE INVENTION

The present disclosure is directed to a bone preparation device.

BACKGROUND

Vertebral endplates have anatomical features that vary among patients. Endplate preparation is often needed to allow an implant (artificial disc, intervertebral spacer, etc.) to closely mate with the vertebral endplate. This can provide a better and more secure fit than would otherwise be obtained.

SUMMARY

In one exemplary aspect, the present disclosure is directed to a bone preparation device for shaping endplates forming an intervertebral disc space between two adjacent vertebrae. The bone preparation device includes a cutter component having a distal end and a proximal end. The cutter component includes a shaft and a cutting blade carried by the shaft and disposed at the distal end of the cutter component. The cutting blade is configured and arranged to form a cut-out in the endplates of the vertebrae. The cutter component also includes a cutter-positioner component having a portion configured to be disposed distal of the cutting blade. The cutter-positioner is arranged to limit the distal travel of the cutter component and to restrict the range of motion of the distal end of the cutter component. The bone preparation device also includes a rotational interface between the cutter component and the cutter-positioner component. The rotational interface is structurally arranged to permit the cutting blade to be rotated at the same time the cutter component is restricted in its range of motion.

In some aspects, the rotational interface includes a protrusion on one of the cutter component and the cutter-positioner component and includes a receiving portion on the other of the cutter component and the cutter-positioner component.

In another exemplary aspect, the present disclosure is directed to a bone preparation device for shaping endplates forming an intervertebral disc space between two adjacent vertebrae. The bone preparation device includes a cutter component and a U-shaped backstop. The cutter component includes a distal end and a proximal end and includes a shaft and a cutting blade carried by the shaft and disposed at the distal end of the cutter component. The cutting blade is configured and arranged to form a cut-out in the endplates of the vertebrae. The cutter component also includes a distal end disposed distally from and spaced apart from the cutting blade. The U-shaped backstop is sized to fit in the intervertebral disc space between first and second adjacent vertebral bodies and configured to be disposed distal of the cutter component. It has a receiving portion disposed therein sized and shaped to receive the distal end of the cutter component. The receiving portion is structurally arranged to permit the distal end of the cutter component to rotate and at the same time restrict the distal end of the cutter from translational movement in at least one direction.

In another exemplary aspect, the present disclosure is directed to a bone preparation device for supporting a cutting instrument that shapes endplates in an intervertebral disc space between two adjacent vertebrae. The bone preparation device includes a U-shaped backstop sized to fit in the intervertebral disc space between first and second adjacent vertebral bodies. The U-shaped backstop includes an open end sized to receive at least a cutting portion of the cutting instrument and a receiving portion structurally arranged to permit a distal end of the cutter component to rotate and at the same time restrict the distal end of the cutter from translational movement in at least one direction.

In some aspects, it includes first and second flange-type fixture elements sized and arranged to engage the sides of the vertebral bodies. The fixture elements have holes formed therein sized to receive screws to fix the backstop in place.

In some aspect, the receiving portion is a slot sized and arranged to receive a protruding portion of the cutting instrument.

BRIEF DESCRIPTION OF THE DRAWINGS

The accompanying drawings serve to exemplify some of the embodiments of this invention.

DETAILED DESCRIPTION

The present disclosure relates generally to the field of orthopedic surgery, and more particularly to instruments and methods for preparing bone for an implantable device. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

This disclosure is directed to instruments and methods for performing spinal surgeries. The shape of vertebral endplates varies from patient to patient and sometimes vertebra to vertebra. In order to properly fit an implant between vertebral bodies and to provide a level of consistency among surgeries, it can be helpful to prepare the endplate by modifying its shape to make it more compatible with the implant. The instruments and methods disclosed herein may be used to cut concavities on superior and inferior endplates to provide a more consistent endplate shape for interfacing with implants.

Figure 1:
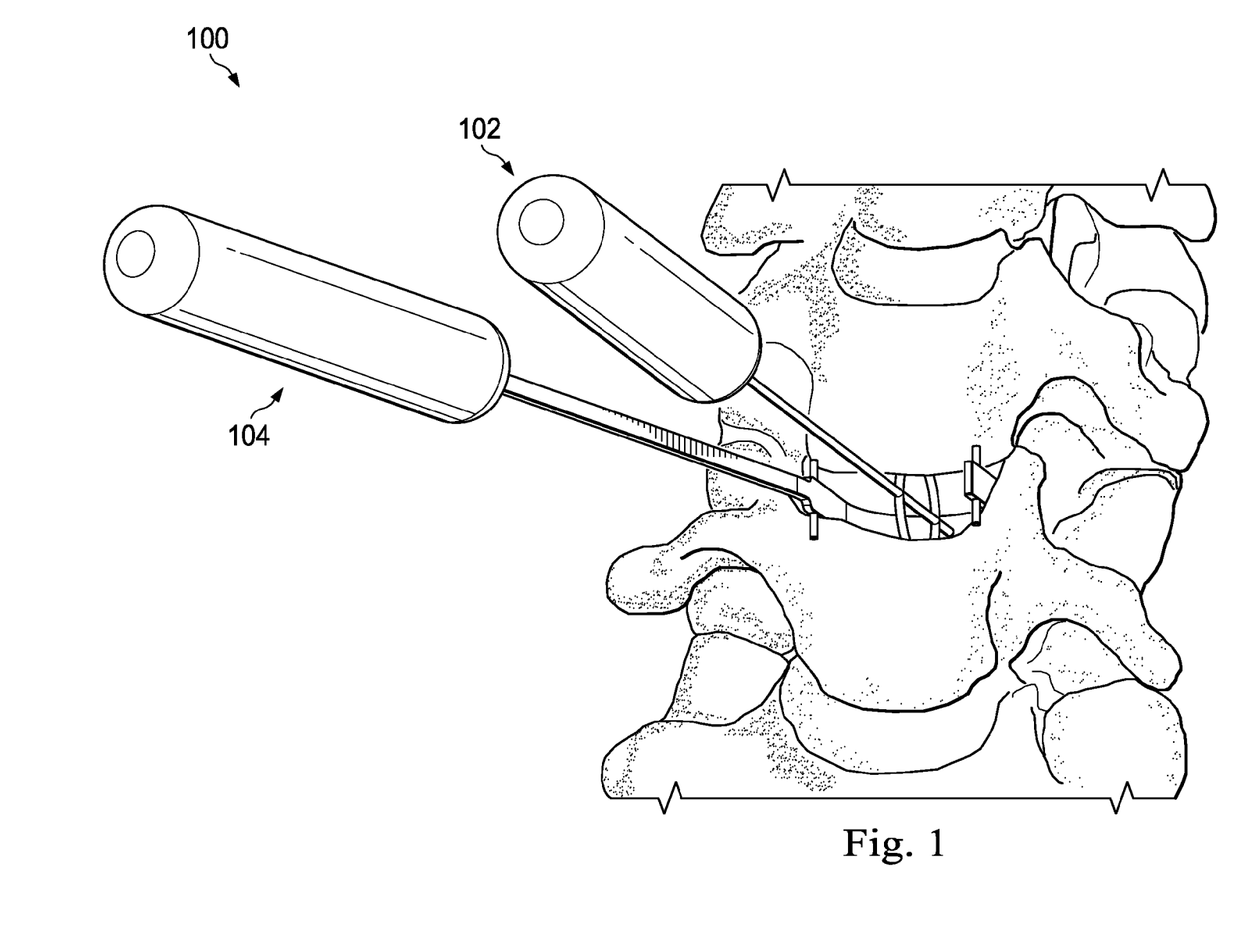
FIG. 1 is an illustration of a perspective view of a portion of a spinal column being treated with the surgical instruments in accordance with an exemplary aspect of the present disclosure.

FIG. 1 illustrates a portion of a spinal column during treatment by the bone preparation device of the present disclosure. The bone preparation device comprises one or more instruments in an instrument set including a cutter 102 and a cutter-positioner 104 engaged to cooperate to modify the endplate shape to a desired profile. In some embodiments, including the one in FIG. 1, the instruments are used through an anterior approach with the cutter-positioner being placed along the posterior edge of the intervertebral disc space. However, other approaches, including anterior, posterior, lateral, anterior-lateral, and posterior-lateral also may be used.

Figures 2, 3:
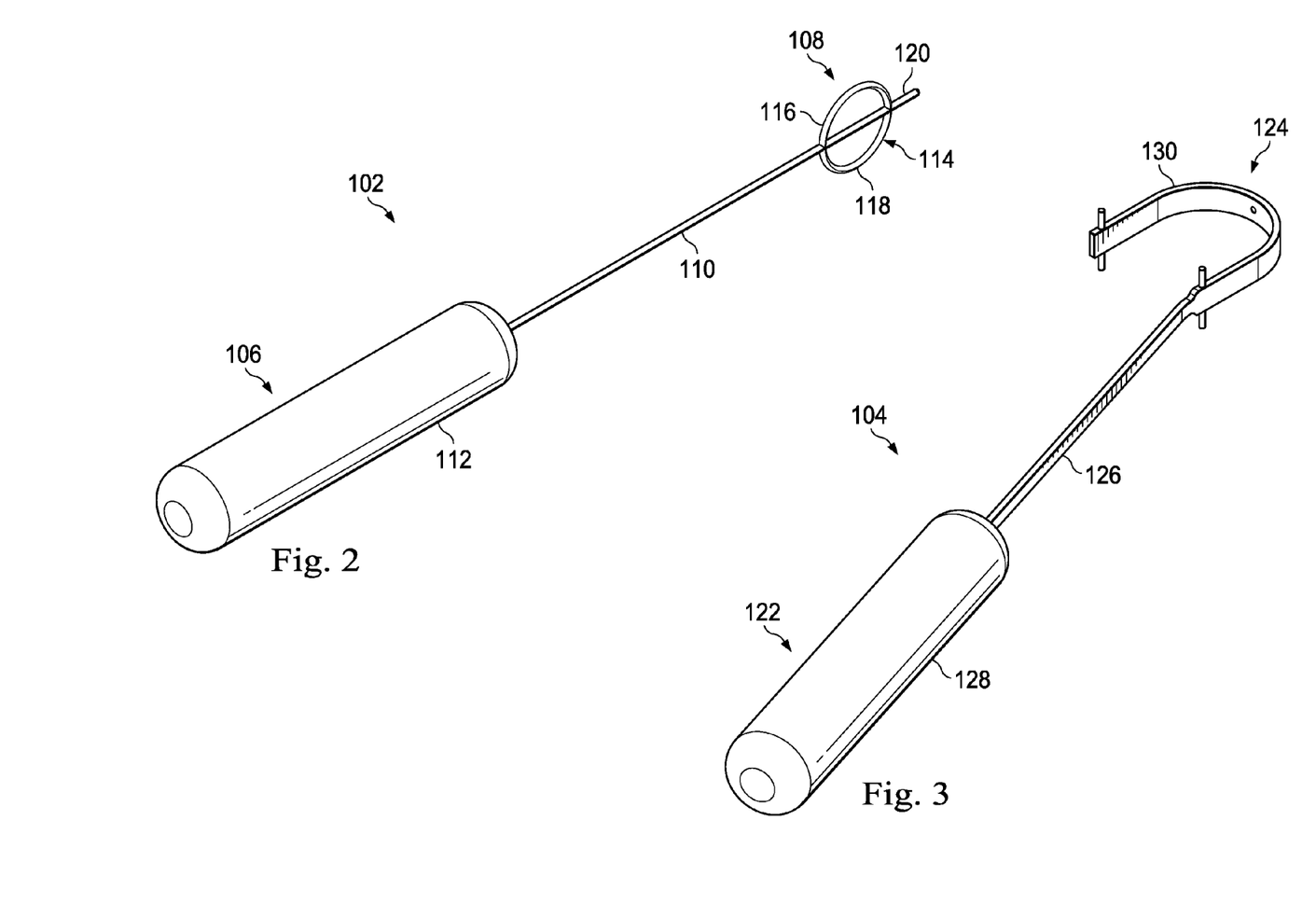
FIG. 2 is an illustration of an exemplary cutter instrument from FIG. 1 in accordance with an exemplary aspect of the present disclosure.
FIG. 3 is an illustration of an exemplary cutter-positioner instrument from FIG. 1 in accordance with an exemplary aspect of the present disclosure.

FIG. 2 shows the cutter 102 in greater detail. The cutter includes a proximal end 106, a distal end 108, and a longitudinally extending shaft 110 extending therebetween. The proximal end 106 includes a handle 112 for gripping and for rotation by a healthcare provider. In this embodiment, the cutter 102 is configured for manual rotation about its axis by its handle 112. However in other embodiments, the cutter 102 is configured to be rotated about its axis by a powered device. This may include an electric motor, hydraulic motor, pneumatic motor, or other motor. In such embodiments the proximal end may be configured for coupling to the working end of the motor.

The distal end 108 of the cutter 102 includes a cutting blade 114. In this embodiment, the cutting blade 114 is a rigid blade formed in a circular shape, symmetrically disposed about the shaft 110. Accordingly, in this embodiment, the cutting blade 114 includes both a first half 116 and a second half 118 opposing each other. As such, when rotated about its shaft 110, the cutter 102 is capable of simultaneously cutting both a top vertebra and a bottom vertebra. In other embodiments however, the cutter 102 includes a cutting blade protruding from only one side of the shaft. In such embodiments, the cutting blade cuts the top and bottom vertebrae one at a time, but can cut both in single revolution of the blade. Other shaped blades are also contemplated, including blades that are cantilevered to connect at only one end, straight blades, and others.

The shaft 110 extends from the handle 112 to the distal end 108. At the distal end 108, the shaft extends distal of the cutting blade 114 and terminates in a protrusion at a distal tip 120. As such, in the embodiment shown, the cutting blade 114 is proximal of and spaced from the distal tip 120 by the distance that the shaft extends beyond the cutting blade.

FIG. 3 illustrates the cutter-positioner 104 in greater detail. Like the cutter 102, the cutter-positioner 104 includes a proximal end 122, a distal end 124, and a longitudinally extending shaft 126 extending therebetween. The proximal end 122 includes a handle 128 for gripping by a healthcare provider.

In this embodiment, the cutter-positioner distal end 124 includes a U-shaped backstop 130 arranged to fit within an intervertebral disc space and form a backstop wall in the disc space. Here, the open end of the U-shaped backstop 130 faces toward the health care provider. Accordingly, when the cutter-positioner 104 is placed within an intervertebral disc space from an anterior approach, the backstop 130 may be placed along the posterior edge of the intervertebral disc space.

The backstop 130 is sized to receive the distal end 108 of the cutter 102. Further, it acts as a placement aid that limits the distance that the cutter 102 can travel into the disc space, helping position the cutter 102 in a suitable location for cutting. In some embodiments, the backstop 130 is sized to generally correspond with the size of the implant to be implanted. Accordingly, in these instances, the backstop 130 also acts as a trial to confirm the implant will fit within the cleared intervertebral disc space.

Figure 4:
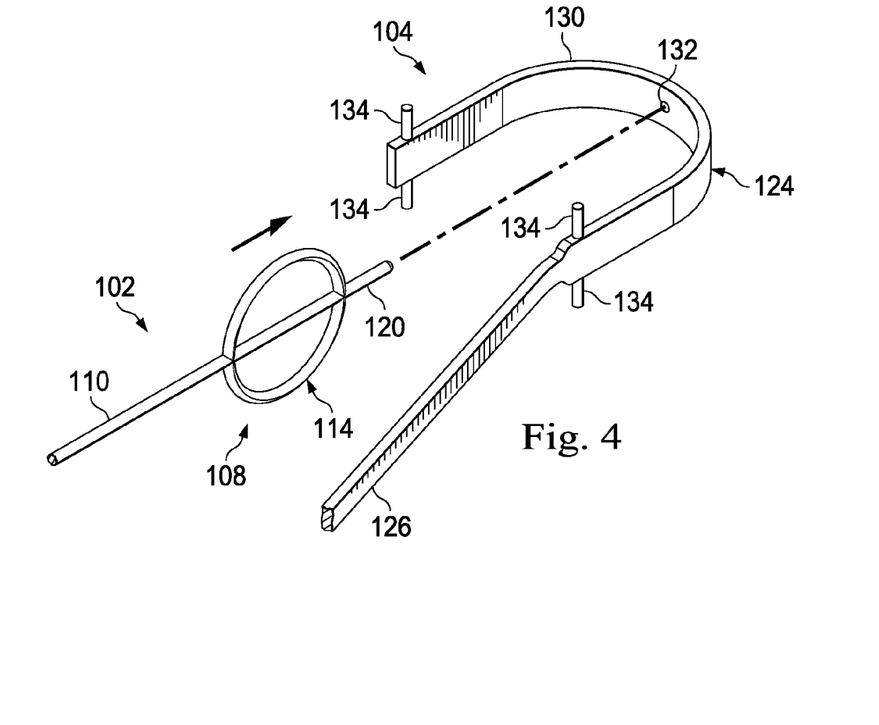
FIGS. 4 and 5 are illustrations of portions the exemplary cutter and cutter-positioner instruments from FIGS. 2 and 3 in accordance with an exemplary aspect of the present disclosure.

FIG. 4 shows the cutter distal end 108 and the backstop 130 in greater detail. To position the cutter 102, the backstop 130 of the cutter-positioner 104 includes a receiving portion forming a part of a rotational interface that in this exemplary embodiment is in the form of a depression 132 sized to receive the distal tip 120 of the cutter 102. The depression 132 serves as an anchoring location for the cutter 102. Accordingly, when engaged, the depression 132 anchors the cutter distal end 108 against undesired lateral or vertical displacement while still permitting the cutter 102 to rotate about its axis and create the desired cavity in the bone.

Accordingly, the depression 132 and the cutter distal tip 120 together create a rotational interface between the cutter 102 and the cutter-positioner 104. The rotational interface is structurally arranged to permit the cutting blade to be rotated relative to the backstop 130 in order to create a cavity in the desired location in the vertebral endplates, and at the same time, the rotational interface restricts the range of motion of the distal tip to a desired range. Here, the rotational interface operates at a single contact point because the depression 132 limits the cutter's range of movement in all side-to-side directions. As indicated by the arrow in FIG. 4, the cutter distal tip 120 is to be inserted into the depression 132.

Still referring to FIG. 4, the backstop 130 also includes positioning features shown as depth stops 134. These are configured to engage surrounding tissue and limit the distance the backstop 130 can be inserted into the intervertebral space. By limiting the depth that the backstop can be inserted into the intervertebral space, the backstop is more easily placed in the desired position.

As shown best in FIG. 4, the cutter-positioner shaft 126 and the backstop 130 connect at an oblique angle. In use, this angle spaces the cutter-positioner handle 128 from the cutter handle 112, as shown in FIG. 1. Accordingly, this provides space for a health care provider to rotate the cutter handle 112 without too much interference by the cutter-positioner handle 128.

Figure 5:
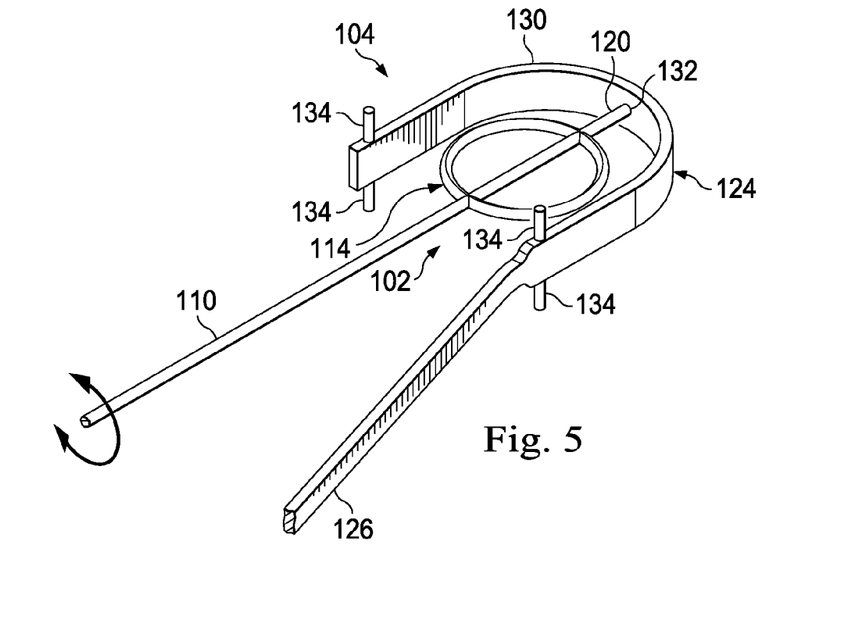

FIG. 5 shows the cutter 102 rotationally interfacing with the cutter-positioner 104. In this example, the rotational interface is the distal tip 120 of the cutter 102 and the depression 132 of the cutter-positioner 104. As can be seen, the cutter 102 engages the cutter-positioner 104 at the rotational interface, which acts as a pivot point to enable the cutter 102 to be rotated 360 degrees about its axis.

Figure 6:
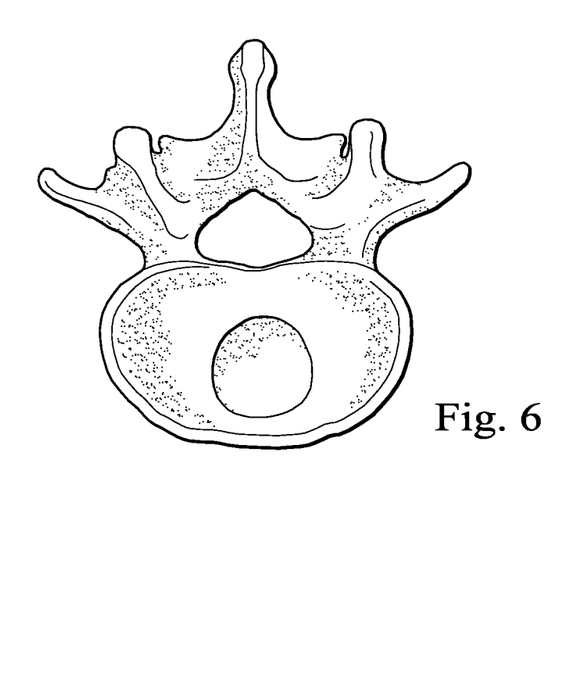
FIGS. 6 and 7 are illustrations of cavities in vertebral bodies made using the principles of the present disclosure.
Figure 7:
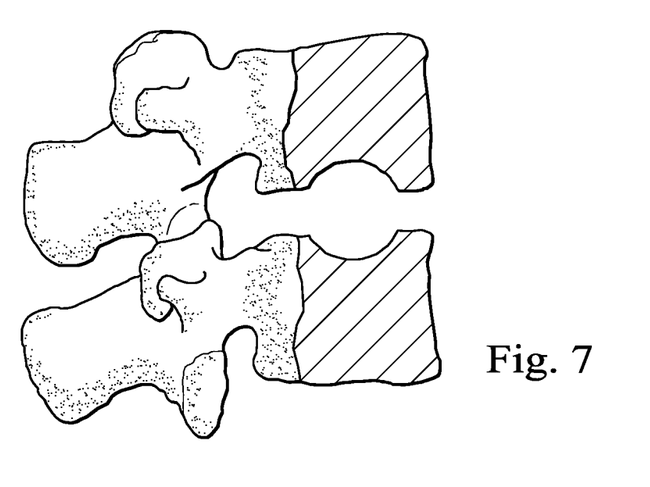

FIGS. 6 and 7 respectively show a cavity formed by the cutter 102 and cutter-positioner 104 in a top view of a vertebral body and a cross-sectioned side view of vertebral bodies. As can be seen, rotation of the cutter 102 in FIG. 2 creates a spherical shaped cavity in the endplates of the upper and lower vertebral bodies.

Figure 8:
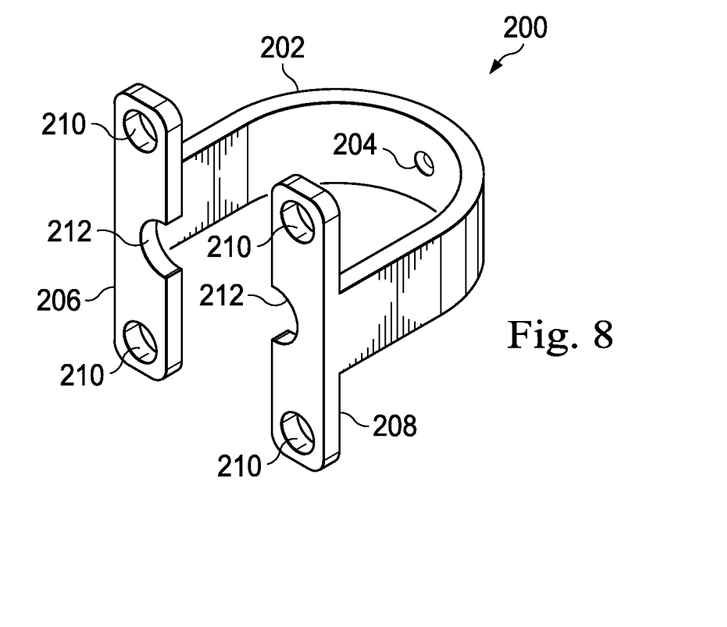
FIGS. 8 and 9 are illustrations of another exemplary cutter-positioner instrument in accordance with an exemplary aspect of the present disclosure.
Figure 9:
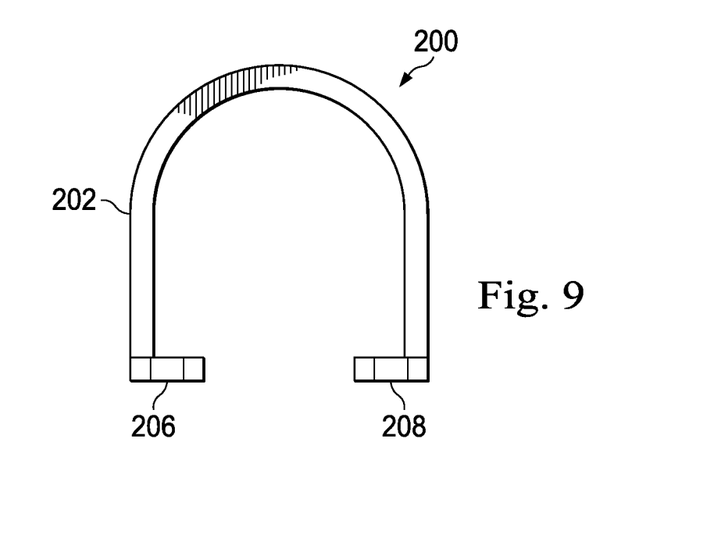

FIGS. 8 and 9 show another embodiment of a cutter-positioner, referenced herein by the numeral 200. Like the cutter-positioner 104 described above, the cutter-positioner 200 includes a U-shaped backstop 202 having a receiving portion in the form of a depression 204. Instead of having a shaft with a handle however, the cutter-positioner 200 is configured to be inserted between adjacent vertebral bodies and held in place by positioning features shown here as flanged fixture elements 206, 208. The fixture elements 206, 208 are configured to abut against the sides of the adjacent vertebral bodies, while the U-shaped backstop 202 extends between the vertebral bodies in the intervertebral disc space. Accordingly, the fixture elements 206, 208 help position the cutter-positioner 200 in the disc space.

In this embodiment, the fixture elements 206, 208 each include two holes 210, located to permit fasteners (not shown) such as bone screws to be driven to the vertebral bodies to fix the cutter-positioner 200 in place during the endplate forming procedure. Other fasteners or other types of securing methods also may be employed.

The cutter-positioner 200 also includes blade accommodating cut-outs 212 in the fixture elements 206, 208 that widen the overall opening. Because of this, a cutter having a blade sized larger than the distance between the fixture elements 206, 208 can still be introduced into the cutter-positioner 200.

Figure 10:
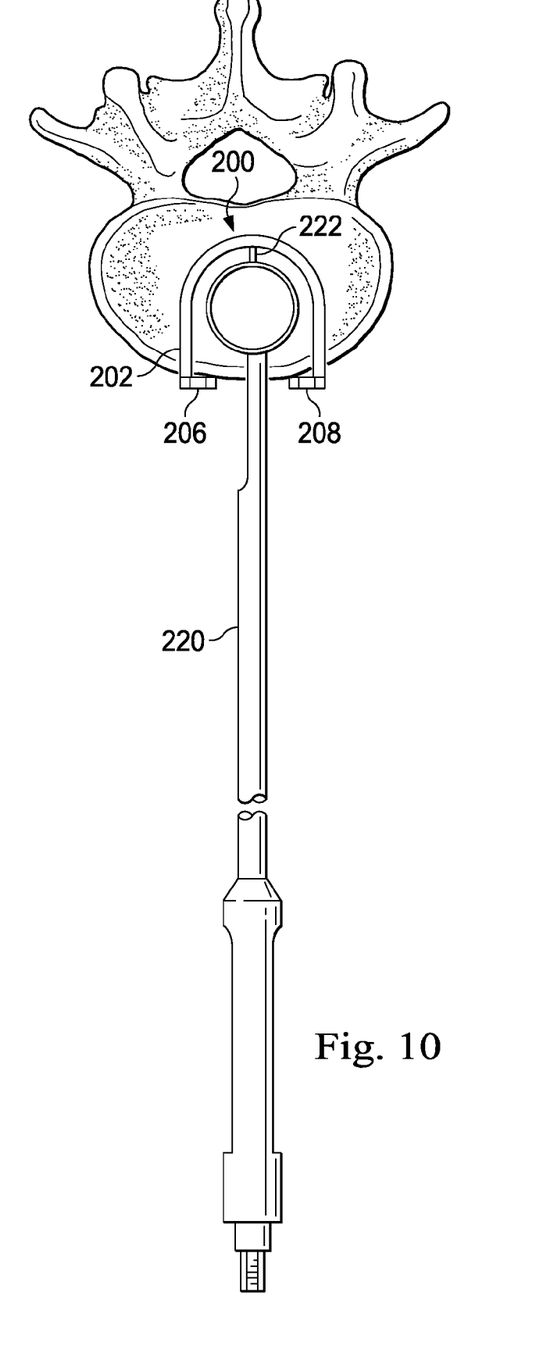
FIGS. 10 and 11 are illustrations of portions of an exemplary cutter instrument and the cutter-positioner instrument from FIG. 8 in accordance with an exemplary aspect of the present disclosure.
Figure 11:
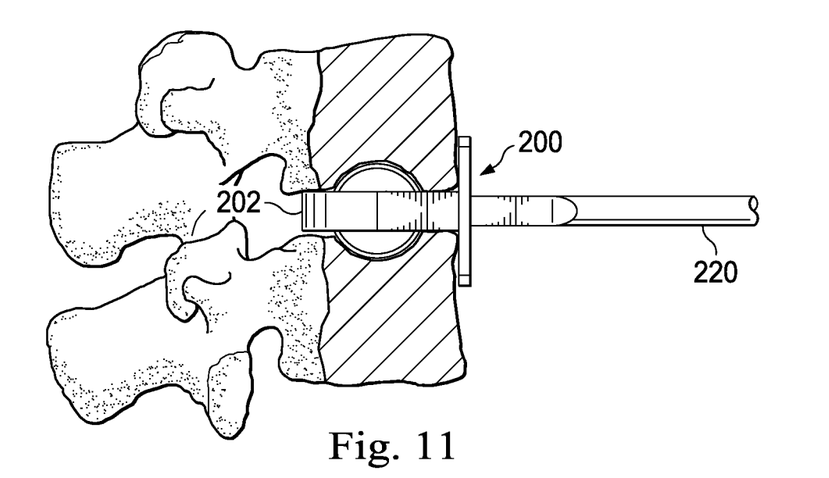

FIGS. 10 and 11 show an exemplary cutter engaged with the cutter-positioner 200 between two adjacent vertebrae. The cutter, referenced herein by the reference numeral 220, is similar to the cutter 102 in many respects, and the description above is applicable to the description here. It is worth noting however that in this embodiment the cutter 220 is formed to cooperate with a removable T-head manual driving handle or cooperates with a powered surgical tool or driver. In addition, the shaft does not extend all the way to the cutter's distal tip, labeled 222. Instead, the protrusion at the distal tip 222 is entirely supported by the blades of the cutter. The offset distance between the blade and distal tip is determined by the length of the rod forming the distal tip 222. As shown in this embodiment, the distal tip 222 is aligned with the longitudinal axis of the shaft. Also as shown, the cutter 220 and the cutter-positioner 200 cooperate at a rotational interface. In this case, the rotational interface is formed by the depression 204 (FIG. 8) and the cutter's distal tip 222.

Figure 12:
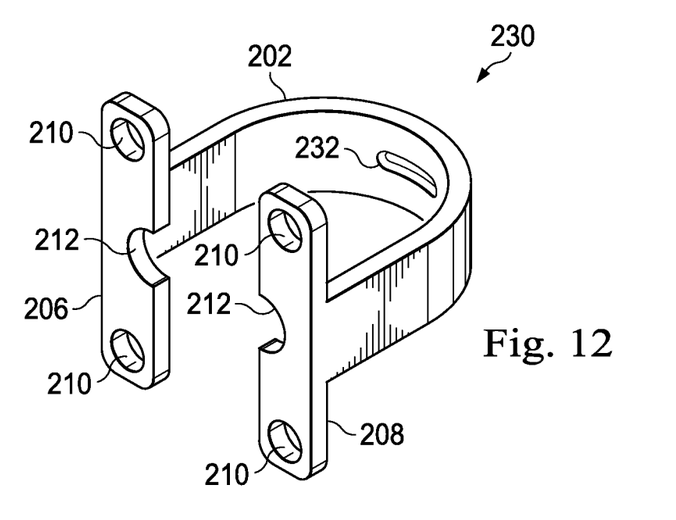
FIGS. 12-17 are illustrations of additional exemplary cutter-positioner instruments in accordance with exemplary aspects of the present disclosure.

FIGS. 12-17 show cutter-positioner embodiments having alternative receiving portions acting as at least a part of the rotational interface that cooperates with the cutter. In these figures, the rotational interface may be formed by indentation (s) in the positioner or may be formed by a through opening. FIG. 12 for example, discloses a cutter-positioner 230 having a receiving portion acting as a rotational interface 232 formed as a horizontal slot. Accordingly, the rotational interface still permits the cutter to rotate relative to the cutter-positioner, but also permits it to translate laterally along the slot. Accordingly, instead of forming a spherical concavity in the vertebral endplates, the resulting concavity has a more elliptical shape.

Figure 13:
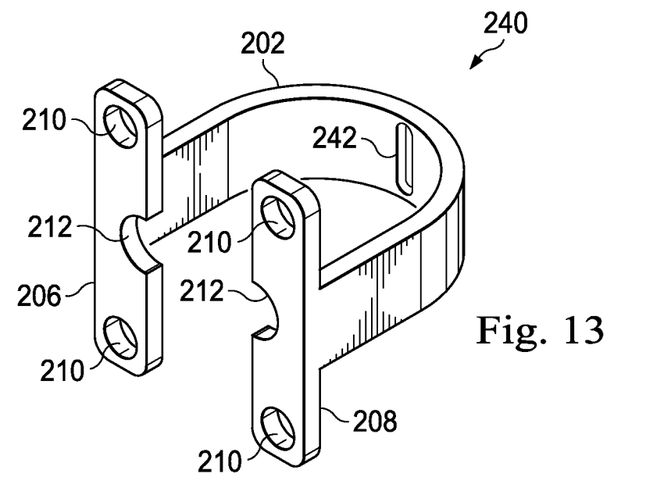

FIG. 13 discloses a cutter-positioner 240 having a receiving portion acting as a rotational interface 242 formed as a vertical slot. Accordingly, the rotational interface still permits the cutter to rotate relative to the cutter-positioner, but also, because the slot forms a track, the slot permits the cutter to translate vertically along the slot. Accordingly, instead of forming a spherical concavity in the vertebral endplates, the resulting concavity has a more elliptical shape in the vertical direction, such that the resulting endplate cut-out is deeper into the endplate.

Figure 14:
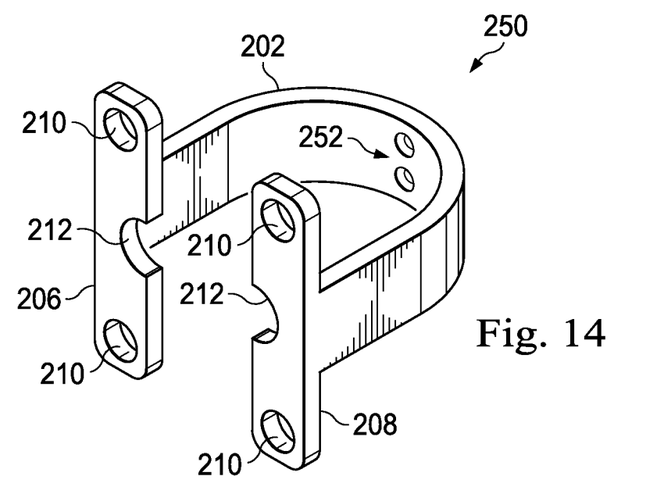

FIG. 14 discloses a cutter-positioner 250 having a receiving portion acting as a rotational interface 252 formed as first and second pivot points, vertically offset from one another. Accordingly, the rotational interface permits the cutter to rotate relative to the cutter-positioner in the first indentation, and permits the cutter to rotate relative to the cutter-positioner in the second indentation. This provides additional cutting depth into the endplate resulting in a cut-out similar to that achieved using the vertical slot. Although shown as vertically offset, the points could be horizontally offset as well. Further, some embodiments include more than two points for engaging the cutter. For example, three, four, or more points may be formed on the cutter-positioner 250.

Figure 15:
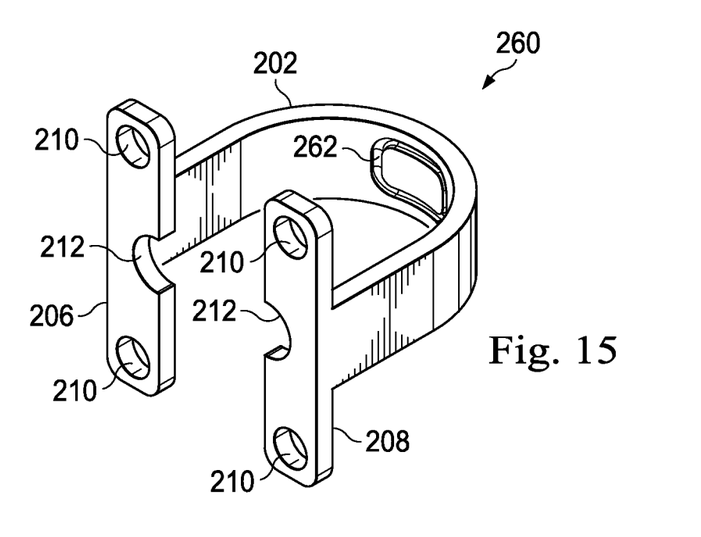

FIG. 15 discloses a cutter-positioner 260 having a receiving portion acting as a rotational interface 262 formed as a rectangular slot or guide. Accordingly, the rotational interface still permits the cutter to rotate relative to the cutter-positioner, but also permits it to translate along the rectangular guide. Accordingly, instead of forming a spherical concavity in the vertebral endplate, the resulting concavity has a more elliptical shape formed deeper into the endplates.

Figure 16:
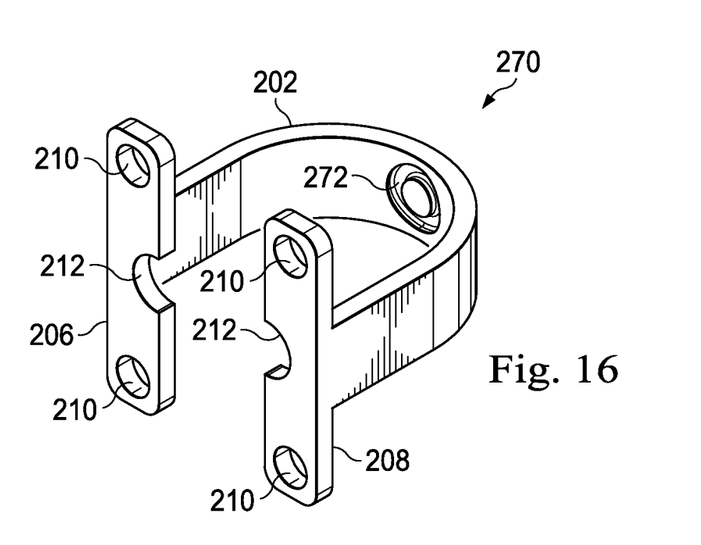

FIG. 16 discloses a cutter-positioner 270 having a receiving portion acting as a rotational interface 272 formed as a circular guide. Accordingly, the rotational interface still permits the cutter to rotate relative to the cutter-positioner, but also permits it to translate along the guide in a circle. Accordingly, a spherical concavity may be formed in the bone tissue having a radius greater than the radius of the cutting blade alone.

Figure 17:
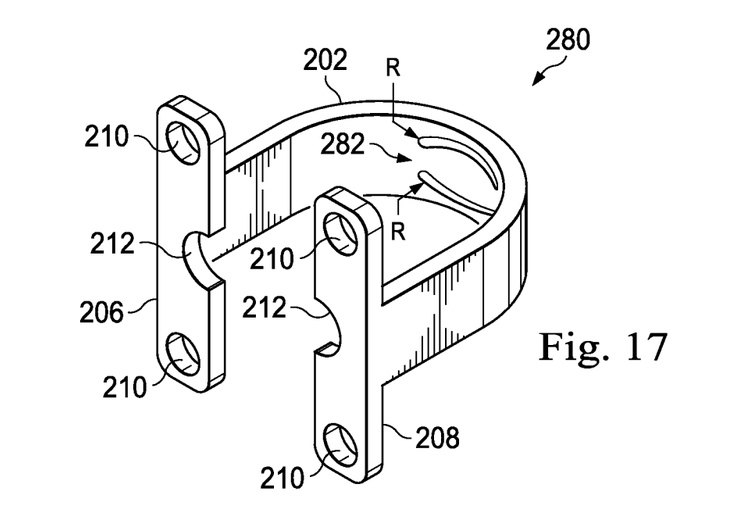

FIG. 17 discloses a cutter-positioner 280 having a receiving portion acting as a rotational interface 282 formed as an oval guide including two slots. Accordingly, the rotational interface still permits the cutter to rotate relative to the cutter-positioner, but also permits it to translate along the two arcs forming the oval. This provides a concavity in the bone having a radius of curvature larger than the radius of curvature of the cutting blade alone.

Figure 18:
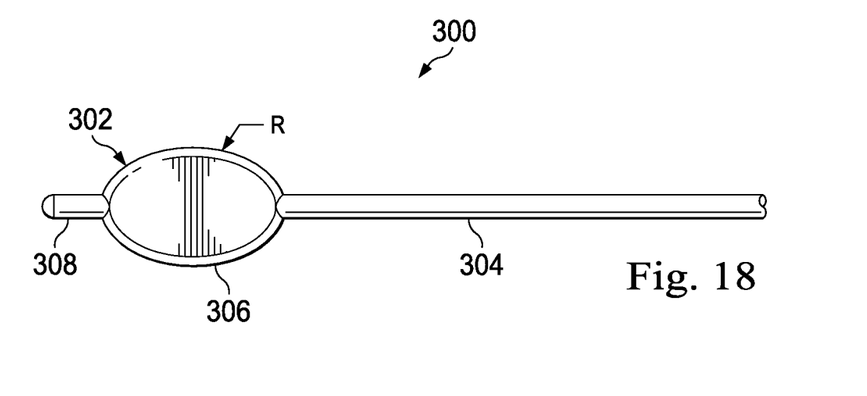
FIG. 18 is an illustration of another exemplary cutter instrument in accordance with an exemplary aspect of the present disclosure.

Although the cutters described above are disclosed as having projecting blades, it should be apparent that any cutter may be used, including cutting burrs. FIG. 18 illustrates one example of a cutting burr that may be employed to cooperate with the cutter-positioners disclosed herein. The cutter, referenced herein by the numeral 300, includes a proximal end (not shown), a distal end 302, and a shaft 304 extending therebetween. The distal end 302 includes a cutting element 306 and a distal tip 308. The distal tip 308 is configured to be received into the corresponding rotational interfacing feature in any of the cutter-positioners disclosed herein in the same manner described and shown with reference to FIGS. 4 and 5. The burr cutter 300 may find particular utility when used with cutter-positioners having slots or guides that permit the cutter to translate while rotating to create the desired endplate profile.

In some embodiments, the cutter 300 has a radius particularly selected to cooperate with the radius of the slots or guides of the cutter-positioners. For example, if the cutter 300 and the guide are particularly configured, the resulting profile formed in the vertebral endplate may be a hemi-spherical concavity. For example, referring to FIGS. 17 and 18, where both the cutter 300 has a radius R in the direction shown, and the slots 282 in the cutter-positioner 280 have a radius R, then the resultant cut in the vertebral endplates will be hemispherical, having the radius R.

Is should be noted that although the cutter-positioners are shown and described as U-shaped, it is worth noting that the backstop 130 need not be completely U-shaped, but in some embodiments, the cutter-positioner extends from one side to only just beyond the rotational interface portion. Also, in some instances, instead of forming a depression in the cutter-positioner, the interface is a through hole, and the distal tip is received into and potentially through the hole. In other embodiments, the backstop includes the projecting tip and the cutter includes the depression that receives the projecting tip. Some embodiments incorporate bearings that aid in the rotation. Other rotational interfaces are also contemplated.

In some embodiments, the cutter-positioners disclosed herein are formed of a radiopaque material for simple viewing under radiographic images. Accordingly, the location of the cutter-positioner may be easily determined. Other cutter-positioner embodiments are formed of a radiolucent material that may include one more radiopaque markers. A radiolucent cutter-positioner provides better viewing of the cutter and the cutter blade under fluoroscopy. Accordingly, a health care provider may more easily determine the actual location of the cut tissue.

In use, a health care provider creates an incision and removes at least a portion of the natural intervertebral disc using conventional methods. The backstop is inserted into the disc space until the positioning features engage the remaining natural intervertebral disc or the vertebral bodies. If the backstop does not fit within the disc space, additional natural disc tissue may be removed or a smaller backstop may be used. Because the backstop may act as a trial for the prosthetic implant that will be placed in the disc space, the health care provider may make note of the size of backstop used.

One placed, depending on the embodiment used, the backstop may be fixed in place to avoid displacement when shaping the endplates. In some embodiments, this may be done by driving screws into positioning features associated with the backstop. In other embodiments, the backstop is held in place by its handle or held in place by frictional engagement with the surrounding tissue. Other ways and methods of fixing the backstop are also contemplated.

Selection of the backstop also may depend on the desired profile of the endplates. For example, the receiving portion, disclosed herein as a depression, hole, or slot, for example, determines the shape or profile of the endplate.

Once the backstop is placed, the cutter may be introduced. It is inserted into the disc space so that its distal end engages and rotationally interfaces with the backstop. As described above, this may be achieved by inserting a protrusion into a receiving portion, disclosed herein as a depression, hole, or slot, for example. In the embodiments shown, the cutter rotates relative to the backstop, but the distal end of the cutter is restrained within the receiving portion from translational movement in at least some directions. Rotating the cutter relative to the backstop cuts the endplate tissue and shapes the vertebral endplates.

Depending on the shape of the receiving portion, it may be necessary to translate the cutter as it rotates or remove it from a first receiving portion and place it in a second receiving portion. When the endplates have been shaped to the desired profile, the cutter and backstop are removed and the implant may by introduced to the intervertebral space.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "top," "upper," "lower," "bottom," "left," and "right," are for illustrative purposes only and can be varied within the scope of the disclosure.

What is claimed is:

1. A bone preparation device for shaping endplates forming an intervertebral disc space between two adjacent vertebrae, compromising:

a cutter component having a distal end and a proximal end, the cutter component comprising:
a shaft having a distal end and a proximal end; and
a cutting blade carried by the shaft and disposed at the distal end of the cutter component, the cutting blade being configured and arranged to form a cut-out in the endplates of the vertebrae;
a cutter-positioner component having a proximal end and a distal end connected by a longitudinal shaft extending between the proximal end and the distal end, a portion configured to be disposed distal of the cutting blade, the cutter-positioner being arranged to limit a distal travel of the cutter component and to restrict a range of motion of the distal end of the cutter component; and
a rotational interface between the cutter component and the cutter-positioner component, the rotational interface being structurally arranged to permit the cutting blade to be rotated at the same time the cutter component is restricted in its range of motion, the rotational interface comprising a protrusion on the cutter component and a receiving portion comprising a pivot depression in the cutter-positioner component, wherein the rotational interface is the distal end of the shaft of the cutter component.

2. The bone preparation device of claim 1, wherein the shaft of the cutter component has a central, longitudinal axis, the distal end being aligned with the longitudinal axis.

3. The bone preparation device of claim 2, wherein the positioner features are flange-type fixture elements sized and arranged to engage the sides of the vertebral bodies.

4. The bone preparation device of claim 1, wherein the cutter-positioner component comprises positioning features that engage with portions of the intervertebral disc or vertebral bodies to limit how far the cutter-positioner component can be inserted into the disc space.

5. The bone preparation device of claim 1, wherein the cutter-positioner comprises a U-shaped backstop and is sized to fit in the intervertebral disc space between the first and second adjacent vertebral bodies.

6. A bone preparation device for shaping endplates forming an intervertebral disc space between two adjacent vertebrae, compromising:

a cutter component having a distal end and a proximal end, the cutter component comprising:
a shaft having a proximal and distal end; and
a single cutting blade carried by the shaft, the cutting blade having a circular shape symmetrically disposed about the shaft, the cutting blade including a first half and a second half opposing each other and disposed at the distal end of the cutter component, the cutting blade being configured and arranged to form a cut-out in the endplates of the vertebrae by simultaneously cutting both a top vertebra and a bottom vertebra when the cutter blade is rotated about by the shaft;
a cutter-positioner component having a proximal end and a distal end connected by a longitudinal shaft extending between the proximal end and the distal end, the cutter positioner having a portion configured to be disposed distal of the cutting blade, the cutter-positioner being arranged to limit a distal travel of the cutter component and to restrict a range of motion of the distal end of the cutter component; and
a rotational interface between the cutter component and the cutter-positioner component, the rotational interface being structurally arranged to permit the cutting blade to be rotated at the same time the cutter component is restricted in its range of motion, wherein the rotational interface comprises:
    a protrusion on the distal end of the shaft of the cutter component; and
    a receiving portion comprising a hole in the cutter-positioner component.

7. The bone preparation device of claim 6, wherein the cutter-positioner comprises a U-shaped backstop configured to have an open end of the U-shaped backstop facing toward a health care provider.

8. The bone preparation device of claim 7, wherein the cutter-positioning component shaft and the backstop connect at an oblique angle.

9. The bone preparation device of claim 8, wherein the cutter-positioner further comprises positioning features that engage with portions of the intervertebral disc or vertebral bodies to limit how far the cutter-positioner component can be inserted into the disc space.

10. A bone preparation device for shaping endplates forming an intervertebral disc space between two adjacent vertebrae, compromising:
    a cutter component having a distal end and a proximal end, the cutter component comprising:
        a shaft having a distal end and a proximal end; and
        a cutting blade carried by the shaft and disposed at the distal end of the cutter component, the cutting blade being configured and arranged to form a cut-out in the endplates of the vertebrae;
    a cutter-positioner component having a proximal end and a distal end connected by a longitudinal shaft extending between the proximal end and the distal end, a portion configured to be disposed distal of the cutting blade, the cutter-positioner being arranged to limit a distal travel of the cutter component and to restrict a range of motion of the distal end of the cutter component; and
    a rotational interface between the cutter component and the cutter-positioner component, the rotational interface being structurally arranged to permit the cutting blade to be rotated at the same time the cutter component is restricted in its range of motion, the rotational interface comprising a protrusion on the cutter component and a receiving portion comprising a slot in the cutter-positioner component, wherein the rotational interface is the distal end of the shaft of the cutter component and the protrusion and the slot are arranged to permit the protrusion to pivot relative to the receiving portion and to translate along the slot.

11. The bone preparation device of claim 10, wherein the slot forms an arc shape.

12. The bone preparation device of claim 11, wherein the cutting blade has a radius of curvature equal to the radius of curvature of the arc shape.

* * * * *